United States Patent [19]

Chait et al.

[11] Patent Number: 4,483,885
[45] Date of Patent: Nov. 20, 1984

[54] METHOD AND DEVICE FOR ELECTROPHORESIS

[75] Inventors: Edward M. Chait; Mary L. Gianelli; Donald R. Johnson, all of Wilmington, Del.

[73] Assignee: E. I. Du Pont de Nemours & Company, Wilmington, Del.

[21] Appl. No.: 548,637

[22] Filed: Nov. 4, 1983

Related U.S. Application Data

[62] Division of Ser. No. 430,836, Sep. 30, 1982, Pat. No. 4,443,319.

[51] Int. Cl.³ .............................................. G01N 27/26
[52] U.S. Cl. ...................................... 427/58; 427/123; 427/125; 427/404; 427/407.1
[58] Field of Search ...................... 204/180 G, 299 R; 427/58, 123, 125, 404, 407.1

[56] References Cited

U.S. PATENT DOCUMENTS

| | | | |
|---|---|---|---|
| 3,715,295 | 6/1973 | Tocci | 204/180 G |
| 3,865,712 | 2/1975 | Davies | 204/299 |
| 4,181,594 | 1/1980 | Rizk et al. | 204/180 G |
| 4,190,517 | 2/1980 | Monthony et al. | 204/299 R |
| 4,297,198 | 10/1981 | Ohishi et al. | 204/299 R |
| 4,305,799 | 12/1981 | Schwarz | 204/180 G |

Primary Examiner—Norman Morgenstern
Assistant Examiner—Richard Bueker

[57] ABSTRACT

A thin film electropheretic device formed of layers with a substrate, electrodes on the substrate and a gel form over both.

2 Claims, 7 Drawing Figures

METHOD AND DEVICE FOR ELECTROPHORESIS

This is a divisional of application Ser. No. 430,836 filed Sept. 30, 1982, now U.S. Pat. No. 4,443,319.

FIELD OF THE INVENTION

This invention relates to a process and a device for effecting electrophoretic separations.

BACKGROUND OF THE INVENTION

Electrophoresis is a well established method for the separation of biochemicals. It is especially useful in the analysis of proteins found as complex mixtures in physiological fluids and tissues. Electrophoretic systems can also be used to separate mixtures of DNA and RNA fragments in the sequencing of macromolecules.

Typically, electrophoresis is carried out in a separation medium such as a gel of agarose or polyacrylamide. These gels are either cast in molds consisting of two glass plates to form a slab or in glass tubes to form a cylindrical gel. Gels are formed in the presence of buffers to control the pH environment of the separation as well as the electrical conductivity of the gel. Simple zonal electrophoresis separates molecules under the influence of an electric field according to their electrophoretic mobility which is a complex function of the charge and size of the protein macromolecule. Isoelectric focusing is an electrophoretic method which uses media not restrictive to the passage of protein and depends on the function of a pH gradient to provide a means for separating proteins on the basis of their isoelectric points. The conventional electrophoresis process may also be modified by the addition of a detergent to the protein mixture and the separating gel to effect a coating of the protein molecule to provide a uniform charge so that separation proceeds only on the basis of molecular weight. Molecular weight separation may also be achieved by adjusting the gel composition to create a network of pore sizes which provides a sieving action to separate the molecules.

In practice, charge and size separation may be combined to increase resolution of the separation of a protein mixture. This process, 2-dimensional electrophoresis, can separate hundreds of components from physiological fluids.

In order to effect the electrophoretic separation, a means for connecting an electric field to the separating gel is needed. Usually this is done by immersing the ends of the gel slab or cylinder in reservoirs of electrically conductive buffer. These are connected by platinum or carbon electrodes immersed in the fluid to the positive and negative terminals of a power supply which establishes a voltage gradient of from 100–3000 V across the separating gel to drive the molecules in the mixture through the gel matrix. This method of attaching the gel to the power supply requires large volumes of buffer to fill the reservoirs, immersion of the gel in buffer or connection via wicks and bulky apparatus for electrophoresis. Care must be taken in making the connection because gasses are released during the separation process. These gases can impair the electrical connection to the gel.

U.S. Pat. No. 3,865,712 issued Feb. 11, 1975 seeks to alleviate the problem of bulkiness and good electrode contact by placing a filter paper wick saturated with a buffer over the gel. Next an electrode is positioned on top of the filter paper. Good contact between the electrode and the filter paper is maintained by the use of a weighted member having toothlike elevations pressing the electrode against the porous material. This has the advantage of permitting easy gas escape during electrophoresis, but in the situation where the wicklike material becomes somewhat dried out, electrical continuity is compromised. Furthermore, this arrangement adds unneeded bulk to the electrophoretic system.

In another effort to solve the problem of providing adequate electrode contact, Tocci in U.S. Pat. No. 3,715,295 issued Feb. 6, 1973 describes an electrophoretic device in which wells are formed at either end of the gel and a semi-solid buffer is placed in the wells over wire electrodes or electrodes which may be painted or printed in the well. While this arrangement is a significant improvement and certainly a step in the right direction it still does not provide a compact, miniaturized package in which good electrical contact with the gel is always maintained. Furthermore, this arrangement does not lend itself to use with the 2D gel electrophoresis techniques now coming into increasing use.

SUMMARY OF THE INVENTION

In accordance with this invention an improved electrophoresis device is formed having a thin film support substrate, a separating gel formed on one face of the substrate, and means for applying an electric potential across at least a portion of the gel characterized by the applying means including spaced electrodes or the substrate integrated into and in electrically conductive contact with the gel, thereby to reduce the bulk of the device.

In various embodiments of the invention, the electrodes are secured to one face of the substrate and the electrodes are formed from thin films of conductive material. Furthermore the electrodes may be polymerically bound to the gel if desired and may be formed in various array configurations to provide various voltage gradients.

In one embodiment of the invention particularly adopted for 2D gel electrophoresis, two different gels are disposed on the same substrate. Each is provided with its own integrated electrodes, the electrode pairs for each gel being positioned transversely of each other for the 2D procedure. In still another embodiment of the invention, a second gel is formed on a first substrate and placed face to face against the gel of a second substrate with a spacer film positioned between the gels. In this manner the 2D electrophoresis may be accomplished by performing the first dimension of electrophoresis in the one gel, removing the spacer film and thereafter performing the electrophoresis in the second gel.

According to the method of this invention an electrophoresis device is constructed by the steps of: forming a sheetlike substrate of a chemically inert material, depositing a thin film of electrically conductive material on two spaced regions of the substrate, and overcoating the film and substrate with a gel electrophoretic polymer material. The electrophoretic device formed by the method of this invention has the advantages of being compact and having electrodes that are integrated with the gel itself so that the problem of poor electrical contact is avoided. The integrated electrodes particularly facilitate 2D gel electrophoretic separations. It reduces the need for buffer solutions and facilitates the proper placement of electrodes. The thin layer gels reduce cooling requirements, permits higher speed separations and increased resolution of components.

BRIEF DESCRIPTION OF THE DRAWINGS

Further advantages and features of this invention will become apparent from the following description wherein.

DESCRIPTION OF THE PREFERRED EMBODIMENT

The various electrophoretic devices constructed in accordance with this invention are designed to permit the use of gels having a relatively thin cross section formed on a substrate of a suitable filmlike material typically 50-500 μm thick. The gel is formed integrally with electrodes that are deposited on the substrate. This has the advantage of providing good electrical contact, low bulk and not requiring the addition of buffer reservoirs, wicks and the like.

Figure 1:
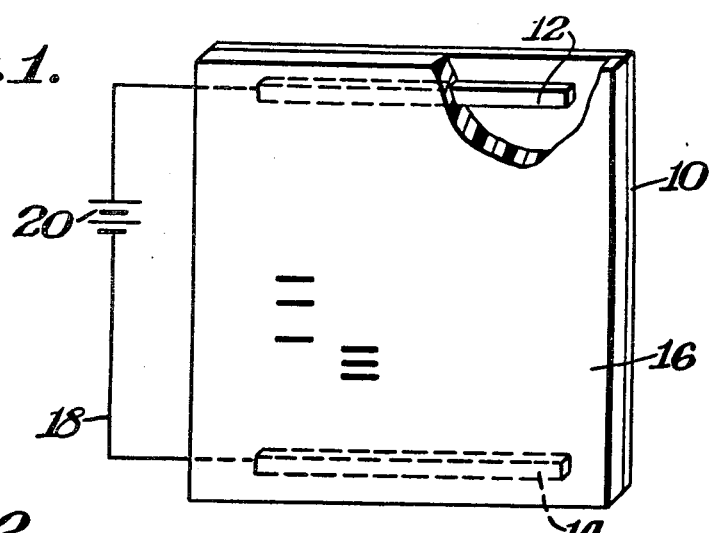
FIG. 1 is a pictorial view of one embodiment of the invention utilizing integrated electrodes in an electrophoretic device.

One embodiment of such a thin layer device is illustrated in FIG. 1 which includes a thin film substrate 10. The substrate may be formed of any of the known materials that are used as supports for electrophoretic gel media and have the characteristics of being chemically inert and having some degree of rigidity sufficient to protect the gel from damage during handling and shipment. It is preferred also that the substrate be transparent. Film materials that are suitable for this purpose include polystyrene, polyethylene, ionomer films sold under the trademark Surlyn ®. Preferably, however, a polyester film such as that sold by E. I. du Pont de Nemours and Company under the trademark Mylar ® is preferred. Glass may also be used as a substrate.

In accordance with this invention, spaced electrodes 12 and 14 are formed along either edge of the substrate 10 so as to be parallel to each other. These electrodes are formed of a thin conductive filmlike material and it may be deposited on the substrate surface 10 by any suitable means such as vacuum deposition, sputtering, or electroless plating. Alternatively the conductive film may be a photopolymer which is formed in a well known technique using a suitable phototool to polymerize the desired electrode portions 12 using actinic radiation, and the undesired excess photopolymer washed away. In still another alternative any of the conductive pastes or inks may be used as desired. Pastes and inks may be deposited on the substrate by printing or silk screening. The electrodes may also be formed as a composite structure with a layer of a good conductor (silver conductive paste) printed first and a second layer of a chemically inert conductor (carbon conductive paste) printed over the silver. This allows the silver to act as a bus bar providing uniform voltage across the length of the electrode.

Preferably, the substrate may be treated with a material to enhance the bond between the substrate and the electrophoresis gel. For example, the polyester film may be treated with a bifunctional carboxylic acid or anhydride or one of the silanes or other materials that will copolymerize with the gel, bonding it to the substrate. The electrodes may be similarly treated.

As the next step in the method of forming the electrophoretic device of FIG. 1 the substrate and electrodes are overcoated with a separating gel to provide a system or a device in which the electrodes are integrated in and in good electrical contact with the gel. The overcoating may take place in a conventional manner in which a mixture of acrylamide in the monomer form and an appropriate initiator in buffer solution are poured into a mold, in which the surface of the substrate with the electrodes forms one wall, and allowed to polymerize in the form of a thin slab. The gels are formed in the presence of buffers so as to control the pH environment of the separation as well as the electrical conductivity of the gel. Since the various gels that are used for electrophoresis are well known, further discussion of the particular gels that may be used is not believed necessary.

After the overcoating of electrodes 12 and 14, electrical connections may be made to the electrodes through wires 18 which are connected to a suitable direct current power supply 20. Needles at the end of the wires 18 may be used to penetrate the gel and make electrical contact with the electrodes 12. The preferred manner in which the wires 18 are connected to the electrodes is depicted in more detail in FIG. 2 in which it is seen that the gel dimensions are foreshortened so that the substrate 10 extends beyond the gel in both directions and the electrodes 12 also extend beyond the separating gel 16 so as to be close to or at the edge of the substrate 10. In this manner simple alligator clips or other connector mechanisms such as electrode edge connectors or spring contacts of known type may be used to connect the power supply to the various electrodes. Another form of electrical contact to the electrodes may be made by platinum contacts forced against the ends of the electrodes which protrude from the edge of the separating gel.

Figure 2:
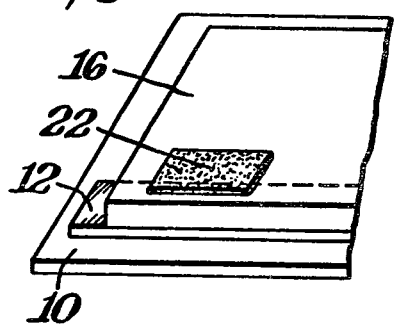
FIG. 2 is a fragmentary pictorial representation of a preferred embodiment of the device of FIG. 1 using a wick to maintain buffer solution at the electrodes.

As may be seen in FIG. 2 it may be desirable in many cases that a paper wick 22, saturated with a suitable buffer solution, be placed on top of the gel 16 in the vicinity of electrodes 12 in order to insure that adequate buffer (and moisture) is available for the required electrical continuity.

It is preferred that the electrodes be formed by silk screening techniques using thick film electronics technology. A typical printed electrode may be in the order of 25 to 100 microns thick. The associated wick typically is 3 millimeters wide and in the order of 70 millimeters long. These electrodes as noted, are placed in parallel regions of the substrate 10 and typically are about 70 millimeters long. Other dimensions may be used as well. Conductive materials that have been successfully used are the Du Pont low temperature curing conductive composition, silver 4929 and nonmetallic conductive materials such as carbon (Atchison Electrodag ® 423SS). Other possibilities include noble metal coatings such as platinum, palladium and gold. These can be combined in composite layers as described previously. Furthermore, carbon has proved to be an especially successful electrode material because it is chemically inert. During use, a small quantity of gas is produced at the electrodes and may either diffuse to the gel surface or can be vented via pinholes formed in the gel substrate.

Figure 3:
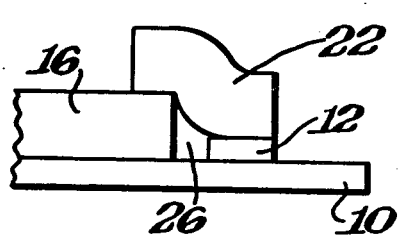
FIG. 3 is a side elevation view of still another embodiment of this invention in which the electrode is integrated with the substrate but separated from the gel.

In another embodiment of the invention, the electrodes 12 may be formed on a substrate 10 outside of the periphery of the gel 16, thereby providing a small gap 26 (FIG. 3) between the edge of the gel and the electrodes 12. This gap facilitates the escape of gases generated during use. To bridge the gap 26, a wick 22, made of a suitable material such as paper and saturated with buffer, may be placed on top of the device so as to bridge the region between the gel 16 and the electrode 12.

Figure 4:
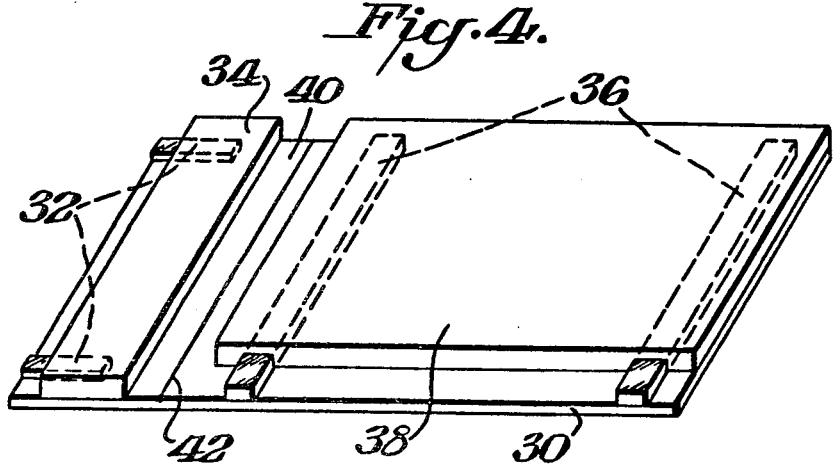
FIG. 4 is a pictorial representation of still another electrophoretic device constructed in accordance with this invention for performing two dimensional electrophoretic separations.

FIG. 4 depicts an alternative embodiment of the invention particularly adapted for 2D electrophoresis. In this instance a rectangular thin film substrate 30 of the type described above is formed with a first pair of short length electrodes 32 at one end in opposing relationship along the width dimension of the substrate. These electrodes are overcoated with one gel 34 such as an isoelectric focusing gel so that isoelectric focussing separations can be effected along the width dimension. In addition, a second pair of electrodes 36 is formed on the remainder of the substrate 30 parallel to the width dimension and along the length dimension. These electrodes 36 are overcoated with a second gel 38 typically used for 2D electrophoresis separations such as a pore size gradient gel with sodium dodecyl sulfate (SDS). A region 40 is left between the two gels 34 and 38 wherein nothing exists except for the substrate thereby to provide an electrical barrier between the two gels. At this point a fold line 42 may be formed in the substrate 30 so as to facilitate folding the first gel 34 over to be in contact with the second gel 38. Folding takes place following the first dimension separation between the electrodes 32. By folding the first gel 34 over to contact the second gel 38, the separated proteins may be contacted with the gel 38 and transferred thereto for the second dimension separation between electrodes 36.

Figure 5:
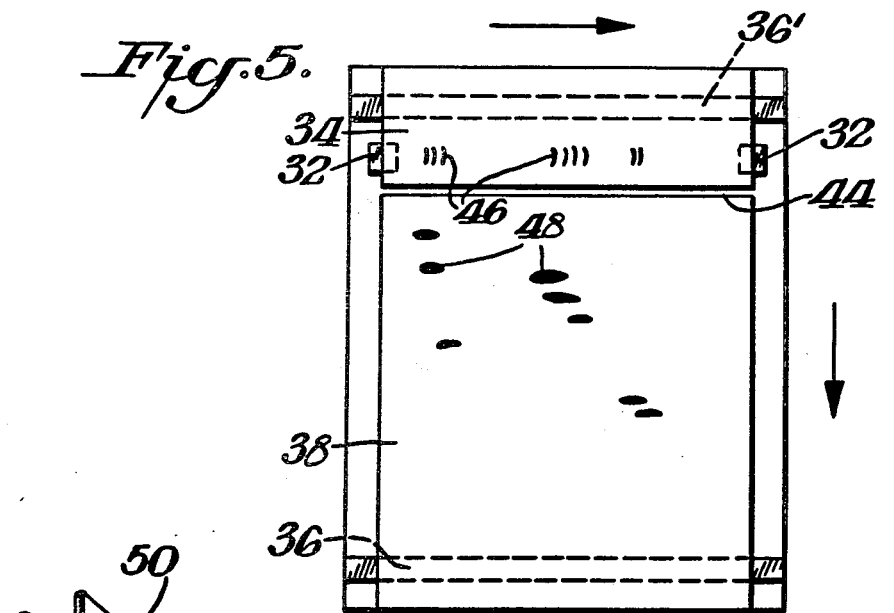
FIG. 5 is a two dimensional electrophoresis device performed constructed in accordance with an alternative embodiment of this invention.

FIG. 5 depicts still another embodiment of the invention also particularly adapted for 2D electrophoresis. In this embodiment, one of the second electrodes, in this instance designated 36' is positioned in the region of the first gel 34. A gel interface or gap 44 is left between the two gels of relatively small dimension. Under these conditions when it is desired to perform the second dimensional separation, the interface gap 44 is simply filled with a buffer solution and the electric gradient established between the electrodes 36, 36'. This does not require the folding or bending of the sheet. In this manner the components 46 separated during the first dimensional separation are passed directly through the buffer solution during the second dimensional separation to provide the second dimension separated components 48.

Figure 6:
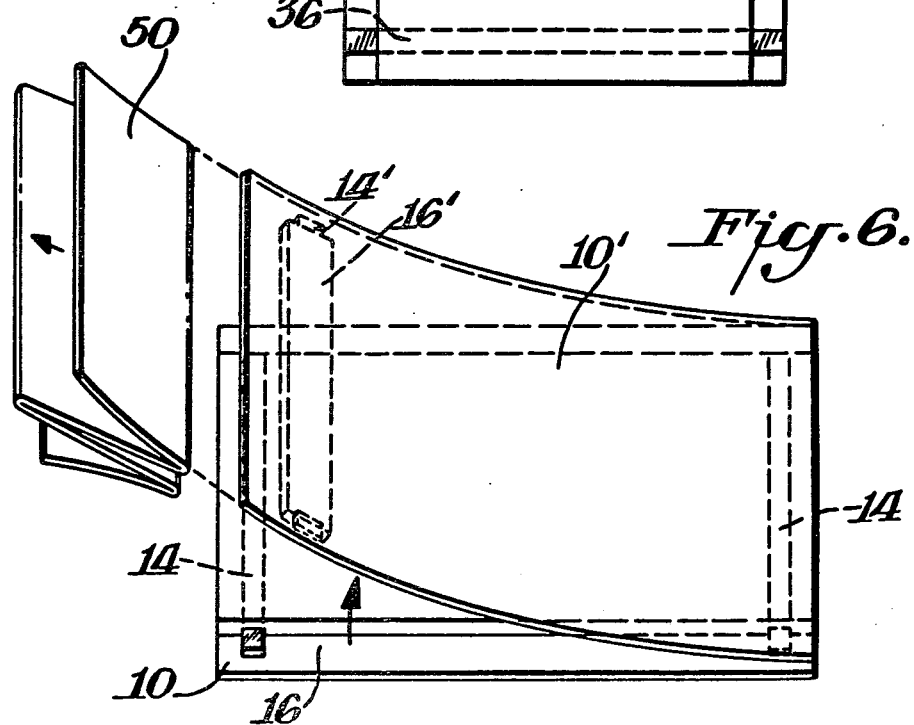
FIG. 6 is a pictorial representation of a two dimensional electrophoretic device constructed in accordance with still another embodiment of this invention.
Figure 7:
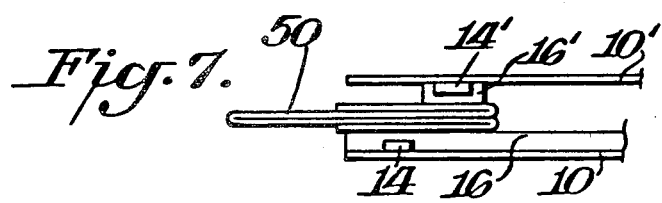
FIG. 7 is a partial side elevation view of the device of FIG. 6.

In a further embodiment of the invention seen in FIGS. 6 and 7, a lower substrate 10 is formed, in the same manner as described in connection with FIG. 1, with one gel 16 and electrodes 14 attached to the first substrate 10 for performing separation along a first dimension. A second substrate 10' having a second dimension gel 16' and corresponding second dimension gel electrodes 14' all on the undersurface is secured at the end remote from the gel 16' to one end of the first substrate 10 as by a clip or bonding (not shown) to form a booklike device. Stated in another manner, the first dimension and second dimension gels 16 and 16' respectively are facing each other. These gels are separated with a spacer member 50 so as to maintain the gels out of contact. The spacer member 50 may be in the form of a W-shaped flexible member that can slip and not adhere to the gels. Polyethylene and polyvinyl chloride films are suitable for this purpose. Using this device, the first dimensional separation is effected in a normal manner. Thereafter the spacer 50 is removed, as by gripping and pulling the center fold thus peeling it away from the gels, permitting the gels to come in contact and transfer the separated components to the second gel. The second dimensional separation is then effected in the usual manner.

It is thus seen that the method and device of this invention has many advantages. For one, the normal large buffer reservoirs required are replaced by the combination of electrodes integrated into the gel and, if required, immobilized buffer in the wicks. Arrays of electrodes may be formed on the gel substrate to allow various types of electrophoresis in multiple dimensions to be carried out in the same gel layer. Multilayer structures of gels and electrodes may be fabricated for moving samples from one gel to another in multidimension separations. The device so formed is complete in itself and requires only the addition of a power supply for operation. The thin layer devices have reduced cooling requirements, permit higher speed separations with increased resolution of components.

We claim:

1. A method of constructing an electrophoresis device comprising the steps of:
   forming a sheetlike substrate of a chemically inert material,
   depositing a thin film of electrically conductive material on two spaced facial regions of the substrates, and
   overcoating the film and substrate with a gel of electrophoretic polymer material.

2. The method of claim 1 which includes the step of coating the conductive films with a crosslinking material which reacts with the gel material.

* * * * *